United States Patent [19]

Schulz et al.

[11] Patent Number: 4,936,899
[45] Date of Patent: Jun. 26, 1990

[54] ABSCISSION OF PARTS OF PLANTS

[75] Inventors: Guenter Schulz, Ludwigshafen; Hubert Sauter, Mannheim; Klaus Grossmann, Neuhofen; Dieter Kleuser, Frankenthal, all of Fed. Rep. of Germany

[73] Assignee: BASF Aktiengesellschaft, Ludwigshafen, Fed. Rep. of Germany

[21] Appl. No.: 339,905

[22] Filed: Apr. 14, 1989

Related U.S. Application Data

[63] Continuation of Ser. No. 133,647, Dec. 16, 1987, abandoned.

[30] Foreign Application Priority Data

Dec. 18, 1986 [DE] Fed. Rep. of Germany ....... 3643246

[51] Int. Cl.$^5$ .................... A01N 25/30; A01N 43/82; A01N 43/40; A01N 33/08
[52] U.S. Cl. .................................. 71/73; 71/DIG. 1; 71/74; 71/70; 71/90; 71/92; 71/94; 71/120; 71/124; 71/121; 71/122
[58] Field of Search ............... 71/DIG. 1, 73, 90, 124, 71/122

[56] References Cited

U.S. PATENT DOCUMENTS

| | | | |
|---|---|---|---|
| 2,547,724 | 4/1951 | Sundholm | 514/442 |
| 3,990,884 | 11/1976 | Barker | 71/DIG. 1 |
| 4,084,956 | 4/1978 | Doyle, Jr. et al. | 71/DIG. 1 |
| 4,130,414 | 12/1987 | Arndt et al. | 71/90 |
| 4,163,658 | 8/1979 | Arndt et al. | 71/73 |
| 4,182,621 | 1/1980 | Ogata et al. | 71/124 |
| 4,294,605 | 10/1981 | Arndt et al. | 71/73 |
| 4,552,582 | 11/1985 | Kruger | 71/90 |

FOREIGN PATENT DOCUMENTS

| | | | |
|---|---|---|---|
| 0024123 | 7/1972 | Japan | 71/124 |
| 0001103 | 1/1985 | Japan | 71/124 |

OTHER PUBLICATIONS

McCutcheon's Emulsifiers & Detergents, 1982, p. 167, "Plurafac".
Lutensol ®-LF types, BASF, Technical Information, M5544d, Jul. 1977.
Lutensol ®-AO types, BASF, Technical Information, TI/P 2588e, Jul. 1986.
Plurafac ®-LF types, BASF, Technical Information, TI/P 2979e, Apr. 1987.
Lutensol ®-ON types, BASF, Technical Information, TI/P 2718e, Aug. 1987.
Product Range–Specialty Chemicals, BASF, FK/P 524e, Sep. 1988.

*Primary Examiner*—Glennon H. Hollrah
*Assistant Examiner*—K. Konstas
*Attorney, Agent, or Firm*—Keil & Weinkauf

[57] ABSTRACT

Agents for the abscission of parts of plants contain one or more urea derivatives of the general formula I

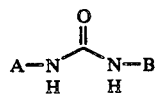

where A is

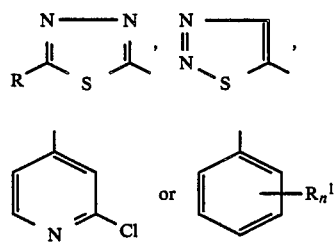

B is cyclopentyl, cyclohexyl or phenyl which is unsubstituted or substituted by one, two or three chlorine, bromine or fluorine atoms, R is hydrogen or methyl, $R^1$ is fluorine, chlorine or, bromine and n is the integer 1, 2 or 3, and either
(a) an oxyethylated tallow fatty amine of the general formula II

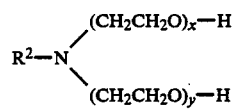

where $R^2$ is $C_{16}$–$C_{18}$-n-alkyl or isoalkyl and x and y together are an integer from 8 to 20, or
(b) a fatty alcohol of the general formula III $$R^3-CH_2O-(CH_2CH_2O)_w-(CH_2CH_2CH_2O)_z-H \qquad III$$

where $R^3$ is $C_{10}$–$C_{18}$-n-alkyl, w is an integer from 3 to 7 and z is an integer from 0 to 7,
the weight ratio of urea derivative I to oxyethylated tallow fatty amine II or fatty alcohol III being from 0.01:1 to 10:1.

3 Claims, No Drawings

ABSCISSION OF PARTS OF PLANTS

This application is a continuation of application Ser. No. 133,647, filed on Dec. 16, 1987 now abandoned.

The present invention relates to novel agents for the abscission of parts of plants, which contain one or more urea derivatives of the general formula I

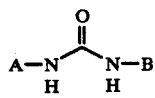

where A is

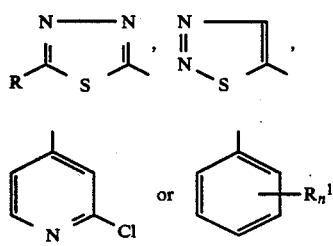

B is cyclopentyl, cyclohexyl or phenyl which is unsubstituted or substituted by one, two or three chlorine, bromine or fluorine atoms, R is hydrogen or methyl, $R^1$ is fluorine, chlorine or bromine and n is the integer 1, 2 or 3, and either (a) an oxyethylated tallow fatty amine of the general formula II

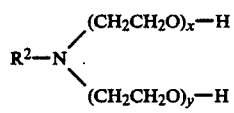

where $R^2$ is $C_{16}$–$C_{18}$-n-alkyl or isoalkyl and x and y together are an integer from 8 to 20, or (b) a fatty alcohol of the general formula III

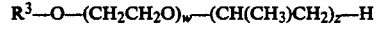

where $R^3$ is $C_{10}$–$C_{18}$-n-alkyl, w is an integer from 3 to 7 and z is an integer from 0 to 7, the weight ratio of urea derivative I to oxyethylated tallow fatty amine II or fatty alcohol III being from 0.01:1 to 10:1.

DE-A-25 06 690 and DE-A-26 19 861 disclose, for example, the compounds I as growth regulators and for defoliating plants. The known agents prepared from them do not contain any oxyethylated tallow fatty amines II or fatty alcohols III. The action of the known agents is unsatisfactory, particularly at low temperatures.

It is also known that polyoxyethylated tallow fatty amines can increase the activity of herbicides, so that lower application rates are sufficient for achieving the same herbicidal effect. However, the manufacturers of such surfactants repeatedly point out that such results are not applicable generally. In a few cases, it has been disclosed that penetration improvers increase the action of fungicides. Increases in activity have been postulated for insecticides. On the other hand, nothing of this type is known in the case of bioregulators, in particular abscission agents (cf. for example Agrochem. Bull. A 85-1; Akzo-Chemie). Moreover, bioregulators occupy a special position among the crop protection agents since the basic active ingredients are not intended to destroy an organism (as, for example, in the case of herbicides, fungicides and insecticides) but influence the development of a plant. It therefore cannot be assumed that the knowledge gained in the case of herbicides, fungicides and insecticides can be extrapolated to bioregulators.

It is an object of the present invention to provide novel agents for defoliating plants, the said agents being based on urea derivatives I and having an improved action even at low temperatures.

We have found that this object is achieved and that the novel additives in the form of oxyethylated tallow fatty amines II and fatty alcohols III improve the abscission of parts of plants by urea derivatives I, even at low temperatures.

Specifically, the substituents in formula I and the substituents and the index in substituent A have the following meanings:

| A | 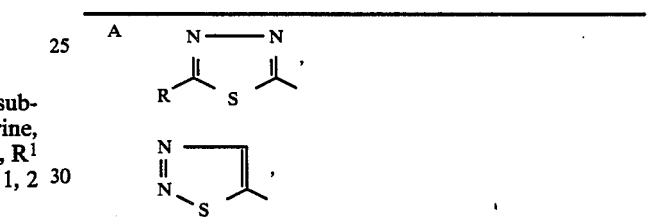 |
|---|---|
|   | 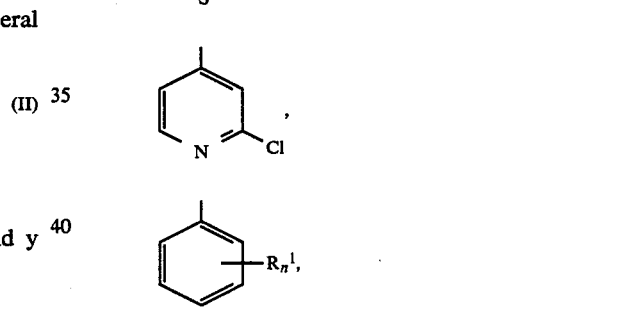 |

B — cyclopentyl,
— cyclohexyl,
— phenyl,
— phenyl which is substituted by 1, 2 or 3 chlorine atoms, such as 2-chlorophenyl, 4-chlorophenyl, 2,4-dichlorophenyl, 2,6-dichlorophenyl and 2,4,6-trichlorophenyl,
— phenyl which is substituted by 1, 2 or 3 bromine atoms, such as 2-bromophenyl, 4-bromophenyl, 2,4-dibromophenyl, 2,6-dibromophenyl and 2,4,6-tribromophenyl,
— phenyl which is substituted by 1, 2 or 3 fluorine atoms, such as 2-fluorophenyl, 4-fluorophenyl, 2,4-difluorophenyl, 6-difluorophenyl and 2,4,6-trifluorophenyl,
R — hydrogen and
— methyl,
$R^1$ — fluorine, chlorine or bromine, and
n — the integer 1, 2 or 3.

Specifically, the substituent and the indices in formula II have the following meanings:

$R^2$—$C_{16}$–$C_{18}$-n-alkyl or isoalkyl, such as n-hexadecyl, isohexadecyl, n-heptadecyl, isoheptadecyl, n-octadecyl and isooctadecyl, x and y—together are an integer from 8 to 20, such as eight, nine, ten, eleven, twelve, thirteen, fourteen, fifteen, sixteen, seventeen, eighteen, nineteen or twenty.

Specifically, the substituent and the indices in formula III have the following meanings:

$R^3$—$C_{10}$-$C_{18}$-n-alkyl, such as n-decyl, n-undecyl, n-dodecyl, n-tridecyl, n-tetradecyl, n-pentadecyl, n-hexadecyl, n-heptadecyl or n-octadecyl, w—an integer from 3 to 7, such as three, four, five, six or seven, and z—an integer from 0 to 7, such as zero, one, two, three, four, five, six or seven.

The abscission of parts of plants, such as leaves, flowers and fruit, from the plant body is a process normally controlled by endogenous substances in the plant. Changes in specific tissue regions located at the base of leaves, flowers or fruit stalks are induced by these plant ingredients. The cells of the separation zone become soft, and mechanical forces, for example gravity or wind, separate the parts of the plant from the plant body (cf. for example Dörffling; Das Hormonsystem der Pflanzen, Georg Thieme Verlag 1982).

The induction of abscission of parts of plants can also be brought about by exogenous active ingredients. The abscission thus induced in a controlled manner is of economic interest and facilitates harvesting, for example of cotton as well as citrus fruit, olives and pomes and stone fruit.

The active ingredients are usually applied in the form of formulations, i.e. with the addition of assistants, such as surfactants. The agents containing the active ingredient and formulation assistants can then be handled by the user in a conventional manner.

The formulations contain in general from 0.1 to 95, preferably from 0.5 to 90, % by weight of active ingredient.

The agents are supplied to the plants mainly by spraying the foliage. Application may be effected, for example, with water as a carrier by a conventional spray technique using about 100–1,000 L/ha of spray liquor. The agents can be used by the low-volume and ultra-low-volume method as well as in the form of microgranules. Because of the good toleration by plants, the application rate of active-ingredient may vary greatly. Rates of from 0.01 to 5 kg/ha are generally sufficient for the treatment of foliage.

The agents can be mixed with other conventional formulation assistants and then used as ready-prepared formulations. They may also be used in the form of an auxiliary, i.e. by the tank mix method. For this purpose, it may be necessary to prepare the auxiliary in the form of a premix in order to ensure homogeneous physical distribution in the spray liquor.

In the Examples below, the particular active ingredients mentioned have been investigated together with appropriate additives.

The active ingredient N-phenyl-N'-(1,2,3-thiadiazol-5-yl)-urea was used in the form of its formulated commercial product (currently available under the trade name DROPP®). The data on the application rate-related action is based in this case on the content of active ingredient. The other active ingredients were converted to similar formulations, after which the novel additives or additives not according to the invention were added.

The following additives are according to the invention:

Oxyethylated tallow fatty amines of the formula II:

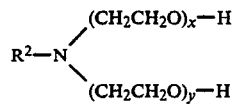

| Designated in the Examples by | Trade name | $R^2$ | x + y |
|---|---|---|---|
| A | Genamin ® T 100 | $C_{16}$-$C_{18}$ | 10 |
| B | Ethomeene ® T 25 | $C_{16}$-$C_{18}$ | 15 |

Fatty alcohol alkoxylates of the formula III:

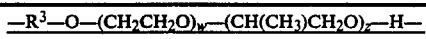

| Designated in the Examples by | Trade name | $R^3$ | w | z |
|---|---|---|---|---|
| C | Plurafac ® LF 700 | $C_{18}$ | 5 | 7 |
| D | Plurafac ® AO 3 | $C_{13}$-$C_{15}$ | 3 | 0 |
| E | Plurafac ® ON 70 | $C_{10}$ | 7 | 0 |

The following assistants are not according to the invention:

AA: nonylphenol-containing assistant, obtainable as Nekanil ® 904

BB: EO/PO block copolymer, obtainable as Pluriol ® PE 6200

CC: tristyrylphenol ethoxylate, obtainable as HOE S 3474

DD: oxyethylated coconut fatty amine of the formula II, but with x+y=2 and $R^2$=$C_{12}$-$C_{14}$, obtainable as Ethomeene ® C 12

EE: fatty alcohol alkoxylate of the formula III, but with w=12, z=6 and $R^3$=$C_{13}$-$C_{15}$, obtainable as Plurafac ® LF 600

FF: acetone

EXAMPLE 1

Active ingredient
N-phenyl-N'-(1,2,3-thiadiazol-5-yl)-urea

Young cotton plants of the Delta Pine variety, at the stage of development of 5–6 developed foliage leaves, were grown under greenhouse conditions (day/ night temperatures 24°/13° C., relative humidity 50–70%), and the leaves were treated, until dripping wet, with aqueous formulations of the stated agents. Five days after application of the agents, the degree of defoliation (untreated control 0%) was determined. The agents were prepared from the commercial product and 0.5% by weight, based on the spray liquor, of the assistants stated in the Table. The application rate of active ingredient was the same in each experiment, the converted application rate being 1 kg/ha and the converted amount of water being 1,000 l/ha, i.e. the concentration of active ingredient in the spray liquor was 0.1%. In the case of the untreated control plants, no dropping of leaves occurred. Result of experiment:

|  | Type of assistant | % defoliation | |
|---|---|---|---|
|  |  | after 5 days | after 7 days |
| Known agent alone | — | 25 | 50 |
|  | A | 50 | 79 |
|  | B | 67 | 85 |
|  | C | 76 | 81 |
|  | D | 59 | 80 |
|  | E | 60 | 92 |

EXAMPLE 2

Active ingredient
N-phenyl-N'-(1,2,3-thiadiazol-5-yl)-urea

Young cotton plants of the Delta Pine variety, at the stage of development of 5 to 6 developed foliage leaves, were grown under greenhouse conditions (day/night temperature 24°/15° C.), and were subjected to foliage treatment, until dripping wet, with aqueous formulations of the agents stated in the Table. Five days after application of the agents, the degree of defoliation was determined as a percentage, based on the untreated control. The agents were prepared from the commercial product DROPP® and added amounts (0.5% by weight, based on the spray liquor) of the assistants stated in the Table. The application rate of active ingredient was the same in each experiment, the converted application rate being 0.5 kg/ha and the converted amount of water being 1,000 l/ha, corresponding to a concentration of active ingredient of 0.5 g/l (0.05%). In the case of the untreated control plants, no dropping of leaves occurred.

| Type of assistant | % defoliation after 7 days |
| --- | --- |
| Known agent alone | 25 |
| A | 90 |
| Comparison DD | 47 |
| C | 84 |
| Comparison EE | 44 |

EXAMPLE 3

Active ingredient
N-cyclopentyl-N'-(1,2,3-thiadiazol-5-yl)-urea

The experiment was carried out as described in Example 1. The agents were prepared by adding, in each case, 50 g of active ingredient to 1 liter of assistant. In the spray liquor, the concentration of assistant was 0.5% by weight. For comparison, conventional formulation assistants are also included in the Table. The application rate of active ingredient was 1 kg/ha (0.1%) in each case. The untreated plants did not drop any leaves during the experiment. The degree of defoliation was determined as a percentage, based on the untreated control.

| Type of assistant | % defoliation after 5 days |
| --- | --- |
| A | 47 |
| B | 93 |
| C | 61 |
| D | 53 |
| Comparison FF | 0 |
| Comparison AA | 10 |
| Comparison BB | 0 |
| Comparison CC | 0 |

The experiments show that, in the case of the type of active ingredient of the formula I, the addition according to the invention results in a substantial increase in the activity and reliability of the action. It is surprising that this effect is pronounced only in the case of the special surfactants of the formulae II and III.

EXAMPLE 4

Active ingredient
N-phenyl-N'-(1,3,4-thiadiazol-2-yl)urea

Young cotton plants were grown as described in Example 1, under greenhouse conditions (day/night temperatures 25°/18° C.), and were treated, until dripping wet, with aqueous formulations of the agents stated in the Table. Five days after application of the agents, the degree of defoliation was determined as a percentage, based on the untreated control. The agents were prepared from the active ingredient and novel assistants as described in Example 3. The amount of active ingredient was the same in each experiment, the converted application rate being 2 kg/ha (0.2%). The untreated plants did not drop any leaves during the experiment.

| Type of assistant | % defoliation after 5 days |
| --- | --- |
| A | 69 |
| B | 77 |
| C | 61 |
| D | 75 |
| Comparison: FF | 0 |

EXAMPLE 5

Active ingredient
N-phenyl-N'-(2-chloropyrid-4-yl)-urea

Young cotton plants were grown as described in Example 1, under greenhouse conditions (day/night temperatures 25°/15° C.), and were subjected to foliage treatment, until dripping wet, with aqueous formulations of the agents stated in the Table. 5 and 8 days after application of the agents, the degree of defoliation was determined as a percentage, based on the untreated control. The agents were prepared from the abovementioned active substance and assistants according to claim 1 or 2, as described in Example D. The application rate of active ingredients was the same in each experiment, the converted application rate being I kg/ha (0.1% strength spray liquor). The untreated plants did not drop any leaves during the experiment.

| No. or name of the assistant | % defoliation after 5 days | after 8 days |
| --- | --- | --- |
| A | 49 | 62 |
| B | 62 | 82 |
| C | 70 | 80 |
| D | 64 | 69 |
| Comparison: FF | 16 | 35 |

We claim:
1. A composition for defoliating cotton plants which comprises an effective amount of N-phenyl-N'-(1,2,3-thiadiazol-5-yl) urea and an effective amount of

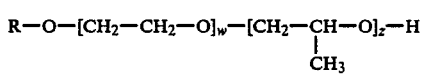

wherein R is a fatty alcohol with 16 to 18 carbon atoms, w is 4 and z is 7 as a potentiating agent.

2. A process for the abscission of parts of cotton plants which comprises: spraying onto the foliage of the plants an effective amount of the composition defined in claim 1.

3. A process for the abscission of parts of cotton plants, which comprises: spraying onto the foliage of said plants from 0.01 to 5 kg per hectare of the composition defined in claim 1.

* * * * *